(12) United States Patent
Ross et al.

(10) Patent No.: US 9,351,714 B2
(45) Date of Patent: May 31, 2016

(54) SYSTEM AND METHOD FOR NON-CONTACT ELECTRONIC ARTICULATION SENSING

(71) Applicant: Covidien LP, Mansfield, MA (US)

(72) Inventors: Adam Ross, Prospect, CT (US);
Michael Zemlok, Prospect, CT (US);
Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 111 days.

(21) Appl. No.: 14/459,008

(22) Filed: Aug. 13, 2014

(65) Prior Publication Data

US 2014/0350530 A1  Nov. 27, 2014

Related U.S. Application Data

(60) Division of application No. 12/942,292, filed on Nov. 9, 2010, now Pat. No. 8,807,414, and a continuation-in-part of application No. 12/345,167, filed on Dec. 29, 2008, now Pat. No. 7,815,090, which (Continued)

(51) Int. Cl.
*A61B 17/04* (2006.01)
*A61B 17/10* (2006.01)
(Continued)

(52) U.S. Cl.
CPC ............ *A61B 17/00* (2013.01); *A61B 17/07207* (2013.01); *A61B 2017/00022* (2013.01);
(Continued)

(58) Field of Classification Search
CPC ................... A61B 2017/00398; A61B 17/068; A61B 2017/00022; A61B 19/44; A61B 2017/00221; A61B 2017/07271

USPC ............. 227/175.1–182.1; 606/139, 142, 143
See application file for complete search history.

(56) References Cited

U.S. PATENT DOCUMENTS 4,566,620 A  1/1986 Green et al.
4,728,020 A  3/1988 Green et al.
(Continued)

FOREIGN PATENT DOCUMENTS

EP  0674876 A2  10/1995
EP  0807408 A1  11/1997
(Continued)

OTHER PUBLICATIONS

European Search Report dated Jul. 28, 2011 for EP 11 15 2266.
(Continued)

*Primary Examiner* — Robert Long

(57) ABSTRACT

A surgical instrument is disclosed. The instrument includes a handle portion, a body portion extending distally from the handle portion and defining a first longitudinal axis and an articulating tool assembly defining a second longitudinal axis and having a proximal end. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The instrument also includes an articulation mechanism configured to articulate the articulating tool assembly, the articulation mechanism including an articulation sensor assembly configured to transmit a sensor signal to a microcontroller which is configured to determine an articulation angle of the articulation assembly.

7 Claims, 9 Drawing Sheets

Related U.S. Application Data is a continuation of application No. 11/544,203, filed on Oct. 6, 2006, now Pat. No. 7,481,348, and a continuation-in-part of application No. 12/189,834, filed on Aug. 12, 2008, now abandoned.

(60) Provisional application No. 61/285,014, filed on Dec. 9, 2009, provisional application No. 60/997,854, filed on Oct. 5, 2007.

(51) Int. Cl.
| | |
|---|---|
| *A61B 17/00* | (2006.01) |
| *A61B 17/072* | (2006.01) |
| *A61B 17/29* | (2006.01) |
| *A61B 17/32* | (2006.01) |
| *A61B 19/00* | (2006.01) |

(52) U.S. Cl.
CPC .......... *A61B2017/00084* (2013.01); *A61B 2017/00137* (2013.01); *A61B 2017/00367* (2013.01); *A61B 2017/00398* (2013.01); *A61B 2017/00734* (2013.01); *A61B 2017/2927* (2013.01); *A61B 2017/320052* (2013.01); *A61B 2019/467* (2013.01)

(56) References Cited

U.S. PATENT DOCUMENTS

| | | | |
|---|---|---|---|
| 4,869,414 A | 9/1989 | Green et al. | |
| 5,247,172 A | 9/1993 | Riemer | |
| 5,312,023 A | 5/1994 | Green et al. | |
| 5,370,650 A | 12/1994 | Tovey et al. | |
| 5,383,888 A | 1/1995 | Zvenyatsky et al. | |
| 5,391,180 A | 2/1995 | Tovey et al. | |
| 5,403,342 A | 4/1995 | Tovey et al. | |
| 5,411,519 A | 5/1995 | Tovey et al. | |
| 5,417,203 A | 5/1995 | Tovey et al. | |
| 5,456,401 A | 10/1995 | Green et al. | |
| 5,482,197 A | 1/1996 | Green et al. | |
| 5,490,819 A | 2/1996 | Nicholas et al. | |
| 5,514,157 A | 5/1996 | Nicholas et al. | |
| 5,526,822 A | 6/1996 | Burbank et al. | |
| 5,560,532 A | 10/1996 | DeFonzo et al. | |
| 5,575,799 A | 11/1996 | Bolanos et al. | |
| 5,578,048 A | 11/1996 | Pasqualucci et al. | |
| 5,607,450 A | 3/1997 | Zvenyatsky et al. | |
| 5,643,294 A | 7/1997 | Tovey et al. | |
| 5,645,209 A | 7/1997 | Green et al. | |
| 5,662,662 A | 9/1997 | Bishop et al. | |
| 5,700,275 A | 12/1997 | Bell et al. | |
| 5,749,893 A | 5/1998 | Vidal et al. | |
| 5,766,205 A | 6/1998 | Zvenyatsky et al. | |
| 5,782,859 A | 7/1998 | Nicholas et al. | |
| 5,785,647 A | 7/1998 | Tompkins et al. | |
| 5,797,538 A | 8/1998 | Heaton et al. | |
| 5,797,959 A | 8/1998 | Castro et al. | |
| 5,823,066 A | 10/1998 | Huitema et al. | |
| 5,865,361 A | 2/1999 | Milliman et al. | |
| 5,901,895 A | 5/1999 | Heaton et al. | |
| 6,241,139 B1 | 6/2001 | Milliman et al. | |
| 6,250,532 B1 | 6/2001 | Green et al. | |
| 6,306,085 B1 | 10/2001 | Farascioni | |
| 6,330,965 B1 | 12/2001 | Milliman et al. | |
| 6,398,725 B1 | 6/2002 | Thompson | |
| 6,565,508 B2 | 5/2003 | Scirica et al. | |
| 6,592,551 B1 | 7/2003 | Cobb | |
| 6,619,529 B2 | 9/2003 | Green et al. | |
| 6,644,532 B2 | 11/2003 | Green et al. | |
| 6,709,389 B2 | 3/2004 | Farascioni | |
| 6,716,232 B1 | 4/2004 | Vidal et al. | |
| 6,716,233 B1 | 4/2004 | Whitman | |
| 6,793,652 B1 | 9/2004 | Whitman et al. | |
| 6,846,307 B2 | 1/2005 | Whitman et al. | |
| 6,846,308 B2 | 1/2005 | Whitman et al. | |
| 6,849,071 B2 | 2/2005 | Whitman et al. | |
| 6,877,647 B2 | 4/2005 | Green et al. | |
| 6,981,628 B2 | 1/2006 | Wales | |
| 6,981,941 B2 | 1/2006 | Whitman et al. | |
| 7,032,798 B2 | 4/2006 | Whitman et al. | |
| 7,077,856 B2 | 7/2006 | Whitman | |
| 7,087,071 B2 | 8/2006 | Nicholas et al. | |
| 7,097,089 B2 | 8/2006 | Marczyk | |
| 7,110,101 B2 | 9/2006 | Schneider | |
| 7,278,563 B1 | 10/2007 | Green | |
| 7,431,188 B1 | 10/2008 | Marczyk | |
| 7,481,348 B2 | 1/2009 | Marczyk | |
| 7,743,683 B2 | 6/2010 | Dayton et al. | |
| 7,743,960 B2 | 6/2010 | Whitman et al. | |
| 7,770,773 B2 | 8/2010 | Whitman et al. | |
| 7,784,663 B2 | 8/2010 | Shelton, IV | |
| 8,157,145 B2 * | 4/2012 | Shelton, IV | A61B 17/07207 227/175.1 |
| 8,807,414 B2 | 8/2014 | Ross et al. | |
| 2003/0014046 A1* | 1/2003 | Edwards | A61B 18/1492 606/41 |
| 2005/0006434 A1 | 1/2005 | Wales et al. | |
| 2005/0131390 A1 | 6/2005 | Heinrich et al. | |
| 2005/0187576 A1 | 8/2005 | Whitman et al. | |
| 2006/0212069 A1 | 9/2006 | Shelton | |
| 2006/0259071 A1 | 11/2006 | Nicholas et al. | |
| 2007/0023477 A1 | 2/2007 | Whitman et al. | |
| 2007/0156019 A1* | 7/2007 | Larkin | A61B 19/2203 600/104 |
| 2007/0175949 A1 | 8/2007 | Shelton et al. | |
| 2008/0083811 A1* | 4/2008 | Marczyk | A61B 17/07207 227/176.1 |
| 2008/0146965 A1 | 6/2008 | Privitera et al. | |
| 2008/0223903 A1 | 9/2008 | Marczyk | |
| 2008/0251568 A1 | 10/2008 | Zemlok et al. | |
| 2008/0255413 A1* | 10/2008 | Zemlok | A61B 17/068 600/106 |
| 2008/0255418 A1* | 10/2008 | Zemlok | A61B 17/068 600/118 |
| 2008/0255607 A1* | 10/2008 | Zemlok | A61B 17/07207 600/127 |
| 2008/0272172 A1* | 11/2008 | Zemlok | A61B 17/07207 227/175.1 |
| 2009/0090763 A1 | 4/2009 | Zemlok et al. | |
| 2009/0108048 A1* | 4/2009 | Zemlok | A61B 17/07207 227/175.1 |
| 2009/0289096 A1* | 11/2009 | Shelton, IV | A61B 17/07207 227/180.1 |
| 2010/0200636 A1* | 8/2010 | Zemlok | A61B 17/07207 227/175.1 |
| 2011/0062211 A1* | 3/2011 | Ross | A61B 17/07207 227/175.1 |
| 2011/0144640 A1 | 6/2011 | Heinrich et al. | |
| 2011/0224518 A1 | 9/2011 | Tindi et al. | |
| 2012/0016362 A1 | 1/2012 | Heinrich et al. | |

FOREIGN PATENT DOCUMENTS

| | | |
|---|---|---|
| EP | 1 769 754 A1 | 4/2007 |
| WO | 03/026511 A1 | 4/2003 |
| WO | 03/030743 A2 | 4/2003 |
| WO | 2009/143092 A1 | 11/2009 |

OTHER PUBLICATIONS

European Search Report for corresponding EP 10252080 application, date of completion is Apr. 8, 2011 (3 pages).

* cited by examiner

SYSTEM AND METHOD FOR NON-CONTACT ELECTRONIC ARTICULATION SENSING

CROSS-REFERENCE TO RELATED APPLICATIONS

The present application is a divisional application of U.S. application Ser. No. 12/942,292, filed on Nov. 9, 2010, which claims the benefit of and priority to U.S. Provisional Application Ser. No. 61/285,014, filed on Dec. 9, 2009, and which is a continuation-in-part application of U.S. application Ser. No. 12/345,167, filed on Dec. 29, 2008, now U.S. Pat. No. 7,815,090, which is a continuation application of U.S. application Ser. No. 11/544,203, filed on Oct. 6, 2006, now U.S. Pat. No. 7,481,348, and which is a continuation-in-part of U.S. application Ser. No. 12/189,834, filed on Aug. 12, 2008, which claims priority to U.S. Provisional Application Ser. No. 60/997,854, filed on Oct. 5, 2007, the entire contents of all of which are hereby incorporated by reference herein.

BACKGROUND

1. Technical Field

The present disclosure relates to a surgical instrument having an articulating tool assembly. More particularly, the present disclosure relates to a surgical instrument which includes a mechanism for actuating an articulating surgical instrument, e.g., a linear stapler, from a non-articulated position, wherein the mechanism includes an articulation sensor assembly.

2. Background of Related Art

Surgical instruments which include a tool assembly mounted on a distal end of a body portion of the surgical instrument for articulation are well known. Typically, such surgical instruments include articulation control mechanisms which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through small incisions in the body to access a surgical site. Typically, an appropriately sized cannula, e.g., 5 mm, 10 mm, etc., is inserted through the body incision to provide a guide channel for accessing the surgical site.

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are known in the art. Certain of these instruments utilize a pressurized gas supply which connects to a trigger mechanism. The trigger mechanism, when depressed, simply releases pressurized gas to implant a fastener into tissue.

Motor-powered surgical staplers are also known in the art. These include powered surgical staplers having motors which activate staple firing mechanisms. However, these motor powered devices only provide for limited user control of the stapling process. The user can only toggle a single switch and/or button to actuate the motor and applies corresponding torque to the stapler's firing mechanisms. In certain other devices, a controller is used to control the stapler.

There is a continual need for new and improved powered surgical staplers which include various sensors. The sensors provide relevant feedback to feedback controllers which automatically adjust various parameters of the powered stapler in response to sensed feedback signals representative of stapler operation, including articulation and actuation of the tool assemblies.

SUMMARY

According to one aspect of the present disclosure, a surgical instrument is disclosed. The instrument includes a handle portion, a body portion extending distally from the handle portion and defining a first longitudinal axis and an articulating tool assembly defining a second longitudinal axis and having a proximal end. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The instrument also includes an articulation mechanism configured to articulate the articulating tool assembly, the articulation mechanism including an articulation sensor assembly configured to transmit a sensor signal to a microcontroller which is configured to determine an articulation angle of the articulation assembly.

According to another aspect of the present disclosure, a surgical instrument is disclosed. The instrument includes a handle portion, a body portion extending distally from the handle portion and defining a first longitudinal axis and an articulating tool assembly defining a second longitudinal axis and having a proximal end. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The instrument also includes an articulation mechanism configured to articulate the articulating tool assembly. The articulation mechanism includes a housing block configured to receive an articulation spindle rotatably housed therein, an articulation link operatively coupled to the articulation spindle, an articulation knob coupled to the articulation spindle for rotating the articulation spindle, wherein rotational motion of the articulation knob is translated into axial motion of the articulation link thereby articulating the articulating surgical tool assembly and an articulation sensor assembly configured to transmit a sensor signal to a microcontroller which is configured to determine an articulation angle of the articulation assembly.

According to another aspect of the present disclosure, an articulation mechanism configured to articulate an articulating tool assembly is disclosed. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The articulation mechanism includes a housing block configured to receive an articulation spindle rotatably housed therein, an articulation link operatively coupled to the articulation spindle and an articulation knob coupled to the articulation spindle for rotating the articulation spindle, wherein rotational motion of the articulation knob is translated into axial motion of the articulation link thereby articulating the articulating surgical tool assembly. The articulation mechanism also includes an articulation sensor assembly configured to transmit a sensor signal to a microcontroller which is configured to determine an articulation angle of the articulation assembly.

BRIEF DESCRIPTION OF THE DRAWINGS

Various embodiments of the subject instrument are described herein with reference to the drawings wherein.

DETAILED DESCRIPTION

Figure 1:
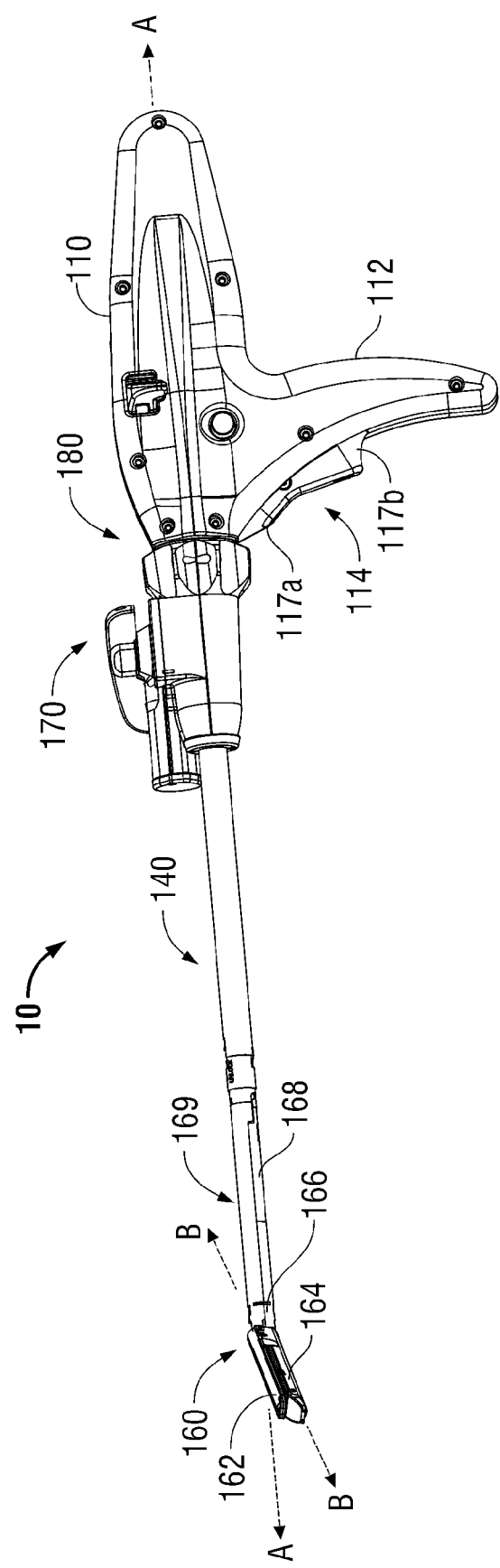
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 10. Referring initially to FIG. 1, powered surgical instrument 10 includes a housing 110, an endoscopic portion 140 defining a first longitudinal axis A-A extending therethrough, and an articulating tool assembly (e.g., end effector 160), defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the components by sterilization processes.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position, in which the anvil assembly 162 is spaced from cartridge assembly 164, and an approximated or clamped position, in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 10, or may be removably attached to the instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A as discussed in more detail below. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, graspers, etc. Such end effectors may be coupled to endoscopic portion 140 of powered surgical instrument 10. An intermediate flexible shaft may be included between handle portion 112 and loading unit. It is envisioned that the incorporation of a flexible shaft may facilitate access to and/or within certain areas of the body.

Figure 2:
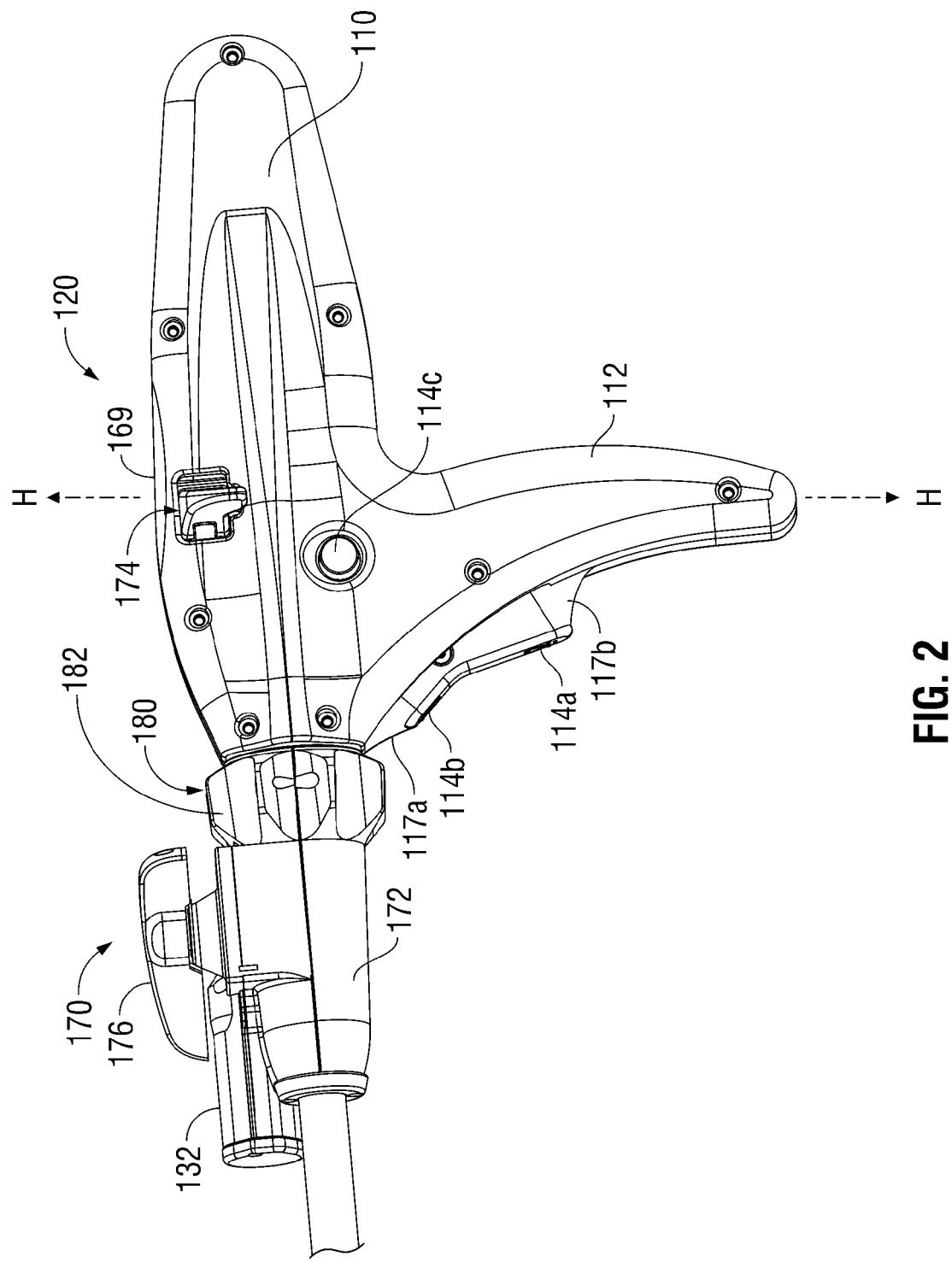
FIG. 2 is a partial enlarged perspective view of the powered surgical instrument according to the embodiment of the present disclosure of FIG. 1.

With reference to FIGS. 1 and 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers.

Figure 4:
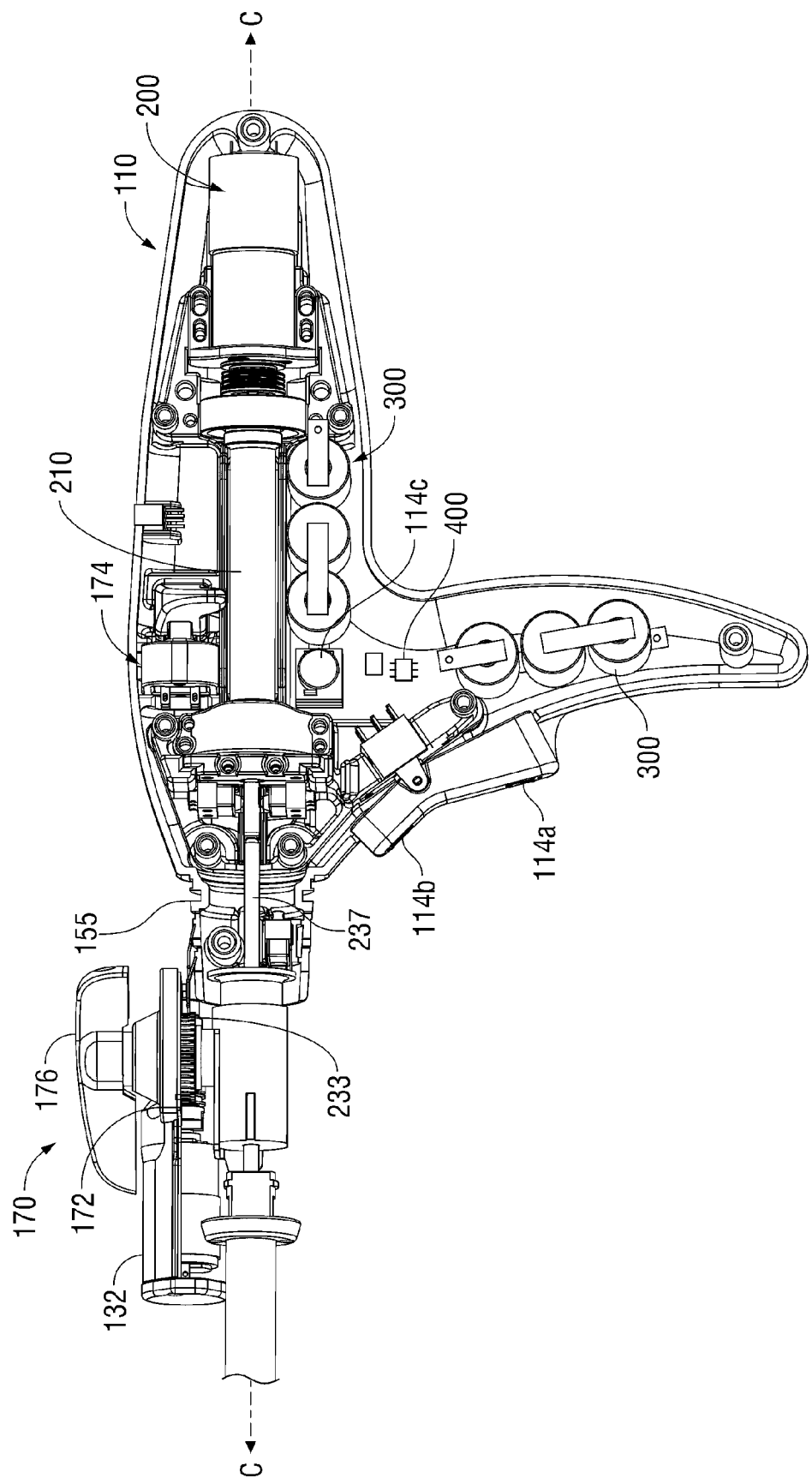
FIG. 4 is a partial perspective sectional view of internal components of the powered surgical instrument of FIG. 1 in accordance with an embodiment of the present disclosure.

Additionally, and with reference to FIGS. 1 and 2, switches 114a, 114b may be used for starting and/or stopping movement of drive motor 200 (FIG. 4). In one embodiment, the switch 114a is configured to activate the drive motor 200 in a first direction to advance firing rod (not explicitly shown) in a distal direction thereby approximating the anvil and the cartridge assemblies 162 and 164. Conversely, the switch 114b may be configured to retract the firing rod to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shield 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod in a non-linear manner. For example, switches 114a, 114b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch 114c is pressed.

The switches 114a and 114b are coupled to a non-linear speed control circuit which can be implemented as a voltage regulation circuit, a variable resistance circuit, or a microelectronic pulse width modulation circuit. The switches 114a and 144b may interface with the control circuit by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as gradually increasing the speed of the drive motor 200 either incrementally or gradually depending on the type of the control circuit being used, based on the depression of the switches 114a and 114b.

Figure 3:
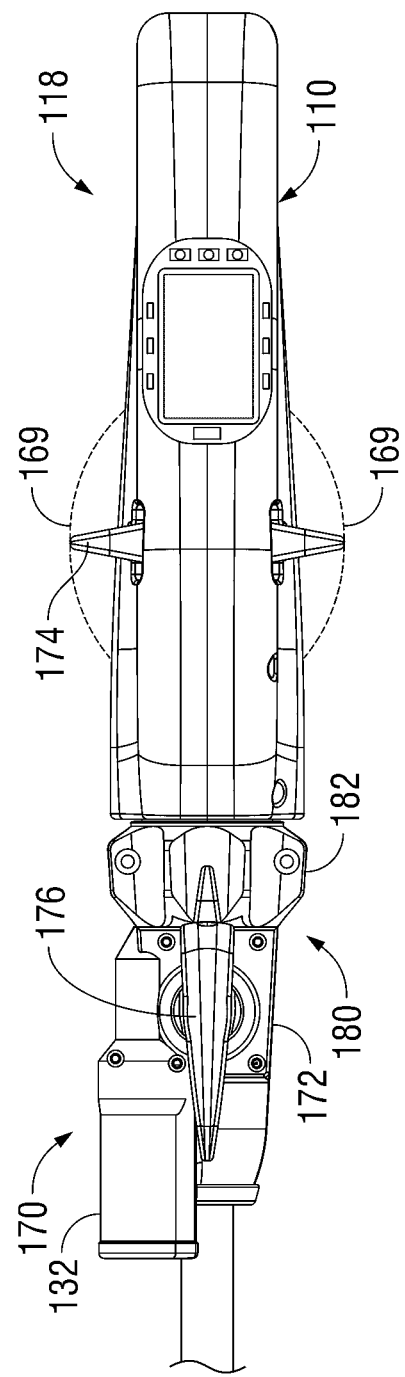
FIG. 3 is a partial enlarged plan view of the powered surgical instrument according to the embodiment of the present disclosure of FIG. 1.

FIGS. 2-4 illustrate an articulation mechanism 170, including an articulation housing 172, a powered articulation switch 174, an articulation motor 132 and a manual articulation knob 176. Translation of the powered articulation switch 174 or pivoting of the manual articulation knob 176 activates the articulation motor 132 which then actuates an articulation gear 233 of the articulation mechanism 170 as shown in FIG. 4. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. The powered articulation switch 174 may also incorporate similar non-linear speed controls as the clamping mechanism. These can be controlled by the switches 114a and 114b.

With reference to FIGS. 2 and 3, the housing 110 includes switch shields 169 having a wing-like shape and extending from the top surface of the housing 110 over the switch 174. The switch shields 169 prevent accidental activation of the switch 174 and require the user to reach below the shield 169 in order to activate the articulation mechanism 170.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus causes corresponding rotation of distal portion 224 of firing rod 220 and end effector 160 about first longitudinal axis A-A. The articulation mechanism 170 is electro-mechanically coupled to one or more conductive rings that are disposed on a housing nose assembly 155 (FIG. 4). The conductive rings may be soldered and/or crimped onto the nose assembly 155 and are in electrical contact with a power source 300 thereby providing electrical power to the articulation mechanism 170. The nose assembly 155 may be modular and may be attached to the housing 110 during assembly to allow for easier soldering and/or crimping of the rings. The articulation mechanism 170 may include one or more brush and/or spring loaded contacts in contact with the conductive rings such that as the housing assembly 180 is rotated along with the articulation housing 172 the articulation mechanism 170 is in continuous contact with the conductive rings thereby receiving electrical power from the power source 300.

Further details of articulation housing 172, powered articulation switch 174, manual articulation knob 176 and providing articulation to end effector 160 are described in detail in commonly-owned U.S. patent application Ser. No. 11/724,733 filed Mar. 15, 2007, the contents of which are hereby incorporated by reference in their entirety. It is envisioned that any combinations of limit switches, proximity sensors (e.g., optical and/or ferromagnetic), linear variable displacement transducers and shaft encoders which may be disposed within housing 110, may be utilized to control and/or record an articulation angle of end effector 160 and/or position of the firing rod 220.

As shown in FIG. 4, the instrument 10 also includes a microcontroller 400 electrically coupled to the motor 200 and various sensors disposed in the instrument 10. The sensors detect various operating parameters of the instrument 10 (e.g., linear speed, rotation speed, articulation position, temperature, battery charge, and the like), which are then reported to the microcontroller 400. The microcontroller 400 may then respond accordingly to the measured operating parameters (e.g., adjust the speed of the motor 200, control articulation angle, shut-off the power supply, report error conditions, etc.).

Figure 5:
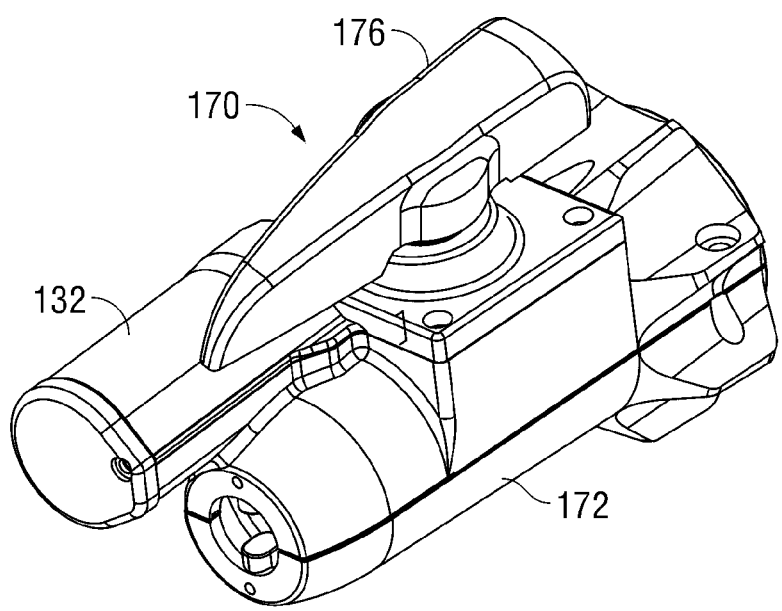
FIG. 5 is a partial perspective view of an articulation mechanism of the powered surgical instrument of FIG. 1 in accordance with an embodiment of the present disclosure.
Figure 6:
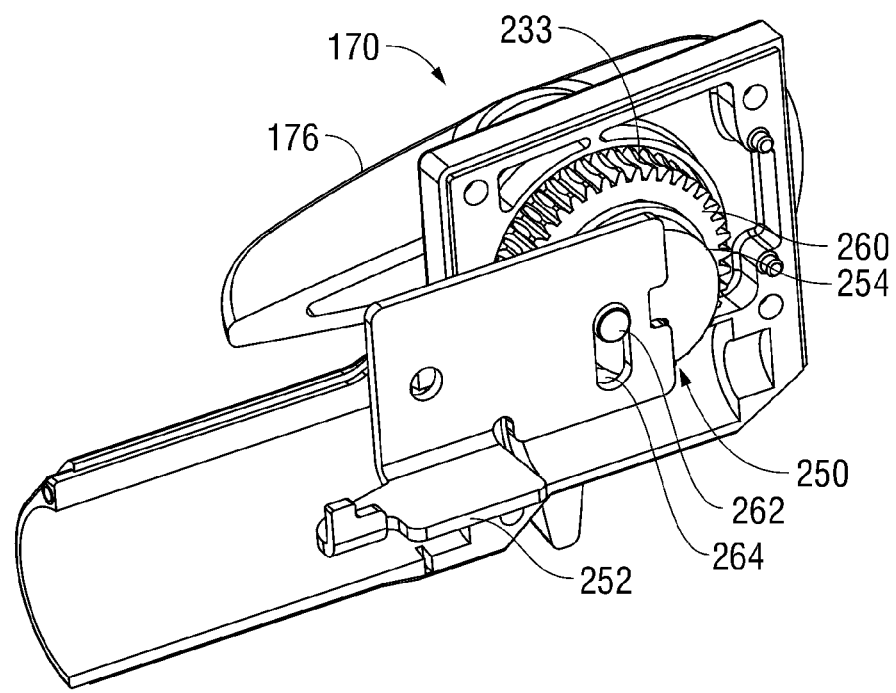
FIG. 6 is a partial perspective sectional view of the articulation mechanism of FIG. 5 in accordance with an embodiment of the present disclosure.

With reference to FIGS. 4-6, the articulation mechanism 170 housed within the articulation housing 172 is shown, which includes the articulation knob 176, an articulation spindle 250, and an articulation link 252 (FIG. 6). The articulation spindle 250 is rotatably housed within the articulation housing 172 and provides a mechanical interface between the articulation knob 176 and the articulation link 252 that interfaces with the end effector 160 to impart articulation thereto. The articulation spindle 250 includes a cylindrical member 254 and a flange 260 disposed on top of the cylindrical member 254 (See FIG. 6). The flange 260 includes the articulation gear 233 and extends laterally from the cylindrical member 254 and has a diameter, which is larger than the diameter of the cylindrical member 254. The articulation gear 233 is coupled to the articulation motor 132, which provides powered or assisted articulation of the end effector 160.

The articulation knob 176 is mounted on top of the articulation spindle 250. This allows for rotational motion of the articulation knob 176 to be translated to the rotational motion of the articulation spindle 250. The longitudinal motion of articulation link 252 is imparted via the rotational motion of the articulation spindle 250. The articulation link 252 mechanically interfaces with the articulation spindle 250 via a link interface member 262 which extends downwardly from a bottom surface of the articulation spindle 250. The articulation link 252 includes an articulation slot 264 which extends laterally across the articulation link 252. The interface member 262 is positioned off center on the bottom surface of the cylindrical member and is received within the slot 264. During rotation of the articulation spindle 250, the interface member 262 is rotated around the center thereof. Since the slot 264 is dimensioned at its width to substantially fit around the interface member 262, the interface member 262 only travels in a lateral direction therein and the longitudinal component of the rotational motion of the interface member 262 is translated to the articulation link 252.

Figure 7:
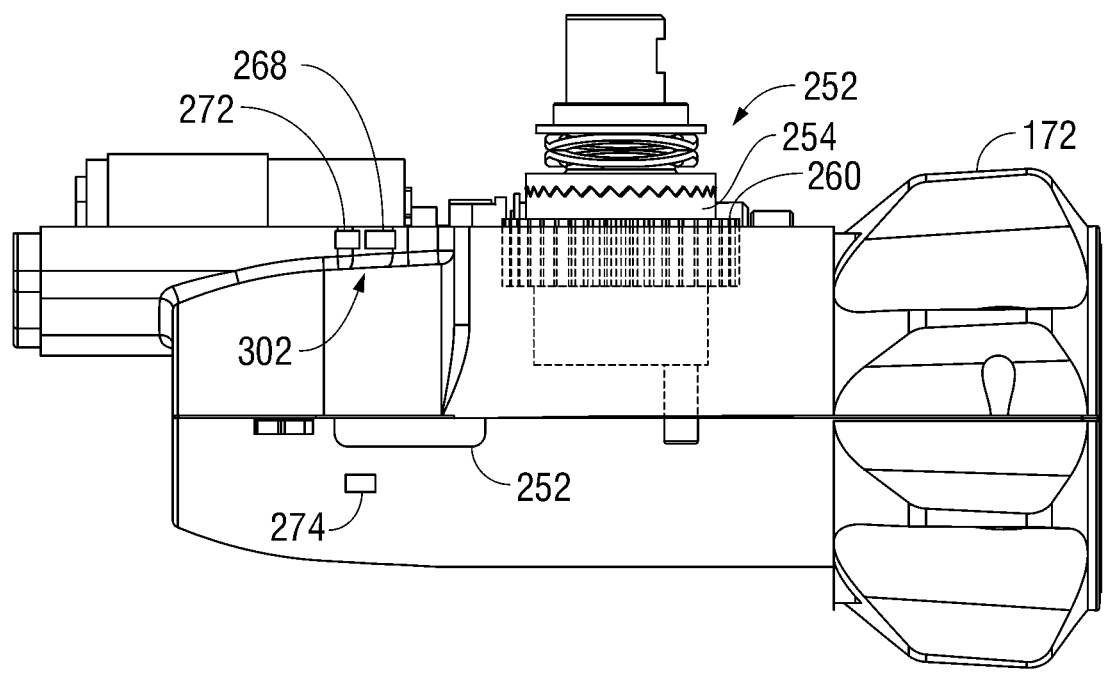
FIG. 7 is a partial side sectional view of the articulation mechanism of FIG. 5 in accordance with an embodiment of the present disclosure.
Figure 8:
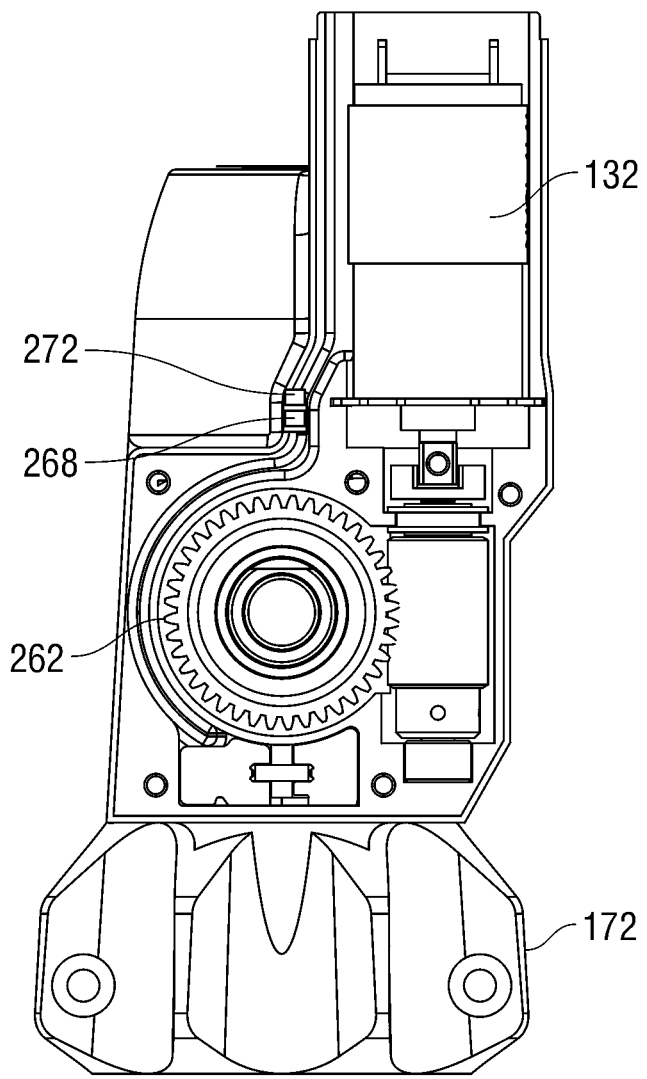
FIG. 8 is a partial top sectional view of the articulation mechanism of FIG. 5 in accordance with an embodiment of the present disclosure.
Figure 9:
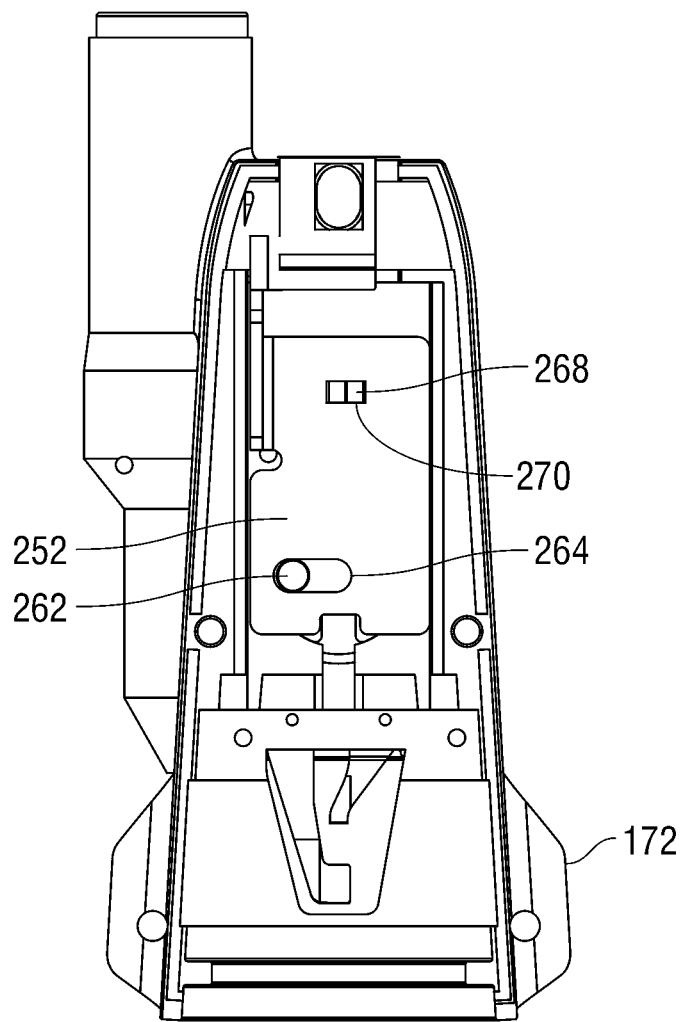
FIG. 9 is a partial bottom sectional view of the articulation mechanism of FIG. 5 in accordance with an embodiment of the present disclosure.

With reference to FIGS. 7-9, the instrument 10 includes an articulation sensor assembly 302 having a photo sensor 268 disposed over (e.g., facing) the articulation link 252. The photo sensor 268 emits a light toward the articulation link 252 and measures properties of the reflected light. The articulation link 252 includes a marker 270 (FIG. 9), which may be a non-reflective mark (e.g., a slot) or a highly reflective mark (e.g., mirrored surface, polished metal, etc.). As shown in FIG. 9, the marker 270 is positioned on the articulation link 252 such that the marker 270 is disposed opposite the photo sensor 268, when the articulation link 252 is at an unarticulated position. The unarticulated position corresponds with the end effector 160 is at an angle of 0° (e.g., aligned with the body portion 168). The photo sensor 268 continually measures the light reflected from the articulation link 252 as the articulation link 252 is moved in the distal direction, when the articulation link 252 is withdrawn to the unarticulated position, the reflected light is modified by the marker 270 (e.g., almost fully reflected or passes therethrough). This allows the photo sensor 268 to measure the 0° position. The photo sensor 268 is coupled to the microcontroller 400 and is configured to transmit a sensed signal corresponding to the changes in the reflected light due to articulation to the microcontroller 400. The microcontroller 400 then determines the articulation angle based on the light measurements transmitted by the photo sensor 268, since the measurements correspond to the displacement of the articulation link 252.

In another embodiment, shown in FIG. 7, the articulation sensor assembly 302 includes a photo emitter 272 and a photo receiver 274 arranged opposite each other on the opposite sides of the articulation link 252. The photo emitter 272 supplies a beam of light toward the photo receiver 274 through the marker 270 when the end effector 160 is at the 0° position. As the articulation link 252 is moved in the distal direction, the marker 270 moves away from the photo emitter 272 and the photo receiver 274 and the articulation link 252 thereby interrupts the beam of light therebetween. The photo sensor 268 and the photo emitter 272 may emit light at any suitable wavelength (e.g., visible spectrum, infrared, etc.).

Figure 10:
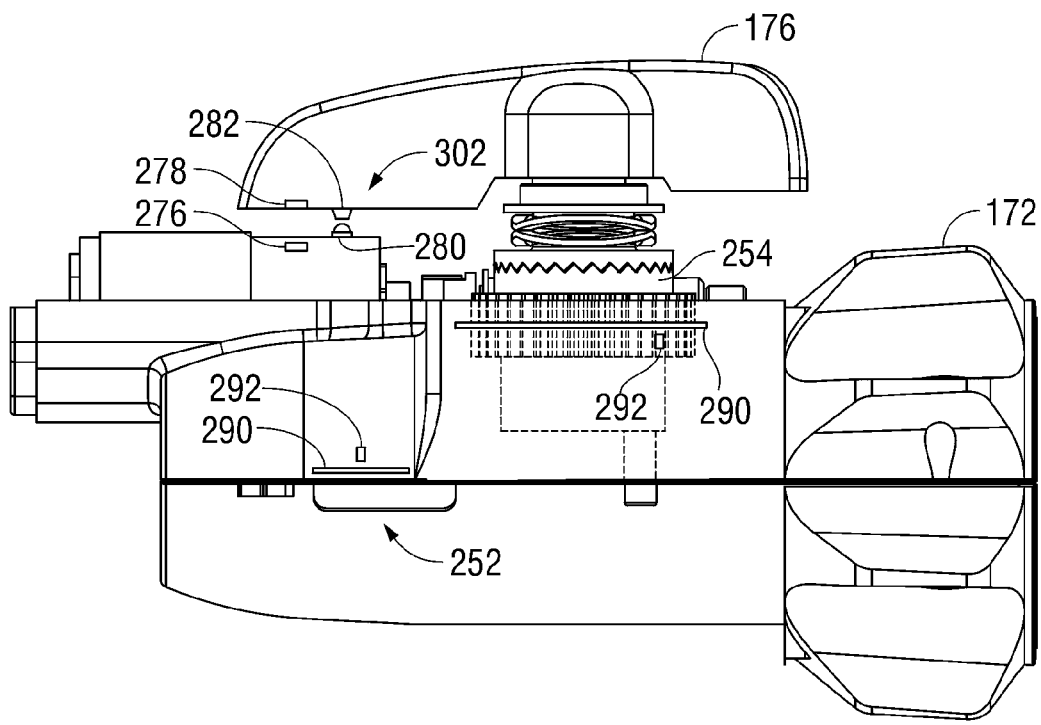
FIG. 10 is a partial side sectional view of the articulation mechanism of FIG. 5 in accordance with an embodiment of the present disclosure.

FIG. 10 illustrates another embodiment of the articulation sensor assembly 302 that includes a magnetic sensor 276 (e.g., Hall-effect sensor) disposed in the articulation housing 172. The sensor 276 is disposed opposite a magnet 278 that is enclosed or otherwise attached to the articulation knob 176. The sensor 276 and the magnet 278 are aligned with respect to each other when the articulation knob 176 is centered and the end effector 160 is at the 0° position. As the articulation knob 176 is rotated to articulate the end effector 160, the magnet 278 is moved from the sensor 276 which correlates the absence and/or decrease in the magnetic field with the articulation of the end effector 160. When the articulation knob 176 is returned to the centered position, the magnet 278 and the sensor 276 are realigned and the sensor 276 determines that the end effector 160 is at the 0° position. The sensor 276 is coupled to the microcontroller 400 and is configured to transmit a sensor signal reflective of the changes in the magnetic field due to the articulation to the microcontroller 400. The microcontroller 400 then determines the articulation angle based on the magnetic field changes as transmitted by the sensor 276, since the measurements are reflective of the articulation of the end effector 160.

FIG. 10 also illustrates another embodiment of the articulation sensor assembly 302 that includes a sensor switch 280 disposed on the articulation housing 282. The switch 280 is disposed opposite a protrusion 282 that is attached to the articulation knob 176. The switch 280 and the protrusion 282 are aligned with respect to each other when the articulation knob 176 is centered and the end effector 160 is at the 0° position. As the articulation knob 176 is rotated to articulate the end effector 160, the protrusion 282 is moved from the switch 280 and the switch 282 is deactivated. When the articulation knob 176 is returned to the centered position, the protrusion 282 and the switch 280 are realigned and the switch 280 is activated which denotes that the end effector 160 is at the 0° position. The switch 280 is coupled to the microcontroller 400 and is configured to transmit the sensor signal reflective of the articulation knob 176 being at the 0° position. The microcontroller 400 then determines that the end effector 160 is in an unarticulated position.

FIG. 10 shows another embodiment of the articulation sensor assembly 302 having a potentiometer 290 disposed on the articulating link 252. The potentiometer 290 is electrically coupled to a contact 292. The contact 292 slides along the surface of the potentiometer 290 as the articulation link 252 is moved in the distal direction due to the rotation of the articulation knob 176. As the contact 292 slides across the potentiometer 290 the position of the contact 292 along the potentiometer 290 adjusts accordingly. The distance the contact 292 moves along the potentiometer 290 is proportional to the degree of articulation of the end effector 160. An initial position of the contact 292 corresponds to the 0° position of the end effector 160. The potentiometer 290 also allows for tracking of the exact angle of articulation.

The potentiometer 290 may also be disposed in a rotational configuration about the spindle 254 allowing the contact 292 to track rotational position of the spindle 254. The contact 292 is aligned at a predetermined position with respect to the potentiometer 290 that corresponds to the 0° position of the end effector 160, allowing the contact 292 to determine the articulation angle of the end effector 160. In one embodiment, the potentiometer 290 may be disposed in indirect contact with the articulation link 252 and/or the articulation spindle 254, such as, via gearing. The potentiometer 290 is coupled to the microcontroller 400 and is configured to transmit a sensor signal reflective of the changes in the electric current due to the rotation of the spindle 254 or displacement of the articulation link 252 to the microcontroller 400. The microcontroller 400 then determines the articulation angle based on the electrical current changes as transmitted by the potentiometer 290, since the measurements are reflective of the articulation of the end effector 160.

Figure 11:
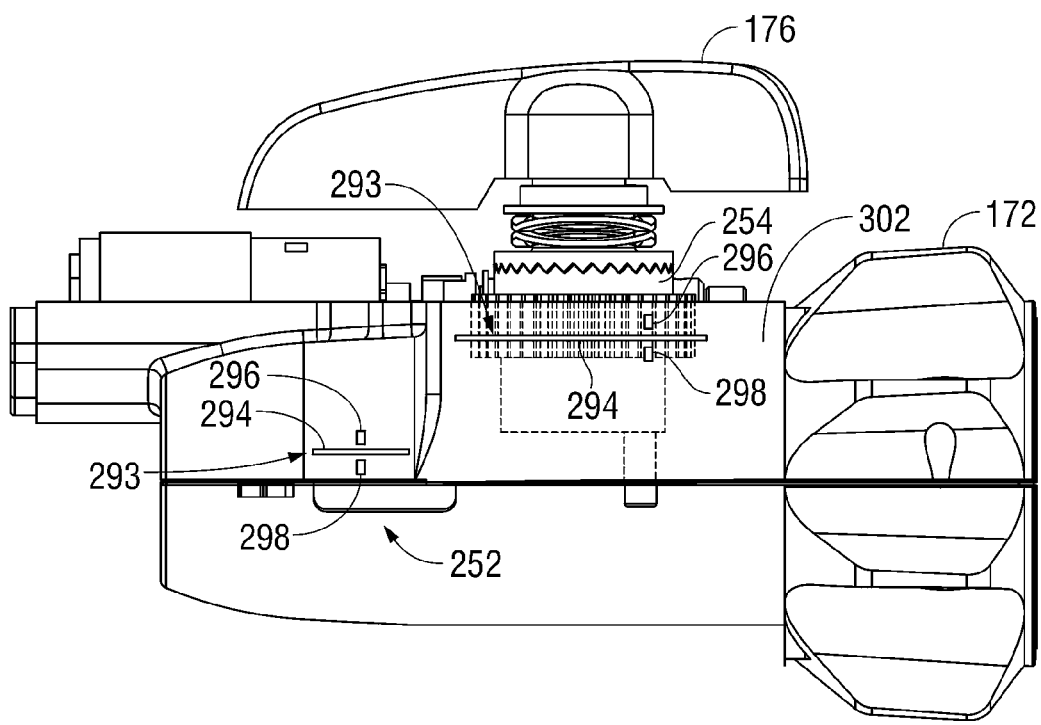
FIG. 11 is a partial side sectional view of the articulation mechanism of FIG. 5 in accordance with an embodiment of the present disclosure.

In another embodiment, as shown in FIG. 11, the articulation sensor assembly 302 includes an optical encoder sensor 293. The encoder sensor 293 includes a linear or rotary encoder 294 and a combination of a photo emitter 296 and a photo receiver 298 arranged opposite each other on the opposite sides of the encoder 294. The photo emitter 296 and receiver 298 are configured to determine the number of interruptions in a light beam which is continuously provided therebetween. As the encoder 294 is translated linearly or rotatably with the articulation of the end effector 160, the photo emitter 296 and emitter 298 measure the number of interruptions in the light beam and rate of occurrences thereof, which allow for determination of the articulation angle of the end effector 160 based on the displacement of the articulation link 252 or the articulation spindle 254. The encoder sensor 293 converts motion into a sequence of digital pulses. By counting a single bit or by decoding a set of bits, the pulses can be converted to relative or absolute position measurements. The encoder sensor 293 is coupled to the microcontroller 400 and is configured to transmit a sensor signal reflective of the motion of the spindle 254 or of the articulation link 252 to the microcontroller 400. The microcontroller 400 then determines the articulation angle based on the electrical current changes as transmitted by the potentiometer 290, since the measurements are reflective of the articulation of the end effector 160.

It will be understood that various modifications may be made to the embodiments shown herein. Therefore, the above description should not be construed as limiting, but merely as exemplifications of preferred embodiments. Although specific features of the powered surgical instrument are shown in some of the drawings and not in others, this is for convenience only as each feature may be combined with any or all of the other features in accordance with the aspects of the present disclosure. Other embodiments will occur to those skilled in the art and are within the following claims.

What is claimed:

1. A surgical instrument, comprising:
   a handle portion;
   a body portion extending distally from the handle portion and defining a first longitudinal axis;
   an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
   an articulation mechanism configured to articulate the articulating tool assembly, wherein the articulation mechanism includes:
   a housing block configured to receive an articulation spindle rotatably housed therein;
   an articulation link operatively coupled to the articulation spindle;
   an articulation knob coupled to the articulation spindle for rotating the articulation spindle, wherein rotational motion of the articulation knob is translated into axial motion of the articulation link thereby articulating the articulating tool assembly; and
   an articulation sensor assembly configured to transmit a sensor signal to a microcontroller which is configured to determine the angle of the articulating tool assembly, wherein the articulation sensor assembly includes a photo sensor that is disposed in spaced relation to the articulation link, the photo sensor configured to illuminate the articulation link and to measure a light reflected from the articulation link and transmit the sensor signal corresponding to the measured reflected light to the microcontroller, wherein the microcontroller is configured to determine the angle as a function of a displacement of the articulation link based on the measured reflected light.

2. A surgical instrument according to claim 1, wherein the articulation link includes a marker at a location that corresponds with an unarticulated position of the articulating tool assembly when the marker is disposed over the photo sensor.

3. A surgical instrument, comprising:
   a handle portion;
   a body portion extending distally from the handle portion and defining a first longitudinal axis;
   an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
   an articulation mechanism configured to articulate the articulating tool assembly, wherein the articulation mechanism includes:
   a housing block configured to receive an articulation spindle rotatably housed therein;
   an articulation link operatively coupled to the articulation spindle;
   an articulation knob coupled to the articulation spindle for rotating the articulation spindle, wherein rotational motion of the articulation knob is translated into axial motion of the articulation link thereby articulating the articulating tool assembly; and
   an articulation sensor assembly configured to transmit a sensor signal to a microcontroller which is configured to determine the angle of the articulating tool assembly, wherein the articulation sensor assembly includes a magnet coupled to the articulation knob and a magnetic sensor coupled to the housing block configured to measure a magnetic field of the magnet and transmit the sensor signal corresponding to the measured magnetic field to the microcontroller, wherein the microcontroller is configured to determine the angle as a function of a displacement of the articulation knob based on the measured magnetic field.

4. A surgical instrument, comprising:
   a handle portion;
   a body portion extending distally from the handle portion and defining a first longitudinal axis;
   an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
   an articulation mechanism configured to articulate the articulating tool assembly, wherein the articulation mechanism includes:
   a housing block configured to receive an articulation spindle rotatably housed therein;
   an articulation link operatively coupled to the articulation spindle;
   an articulation knob coupled to the articulation spindle for rotating the articulation spindle, wherein rotational motion of the articulation knob is translated into axial motion of the articulation link thereby articulating the articulating tool assembly; and
   an articulation sensor assembly configured to transmit a sensor signal to a microcontroller which is configured to determine the angle of the articulating tool assembly, wherein the articulation sensor assembly includes a sensor switch coupled to the housing block configured to interface with a protrusion coupled to the articulation knob, such that the protrusion actuates the sensor switch when the articulation knob is centered and the sensor switch transmits the sensor signal to the microcontroller, wherein the microcontroller is configured to determine whether the articulating tool assembly is in the first position.

5. A surgical instrument, comprising:
a handle portion;
a body portion extending distally from the handle portion and defining a first longitudinal axis;
an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
an articulation mechanism configured to articulate the articulating tool assembly, wherein the articulation mechanism includes:
a housing block configured to receive an articulation spindle rotatably housed therein;
an articulation link operatively coupled to the articulation spindle;
an articulation knob coupled to the articulation spindle for rotating the articulation spindle, wherein rotational motion of the articulation knob is translated into axial motion of the articulation link thereby articulating the articulating tool assembly; and
an articulation sensor assembly configured to transmit a sensor signal to a microcontroller which is configured to determine the angle of the articulating tool assembly, wherein the articulation sensor assembly includes a potentiometer electrically coupled to a contact that is coupled to at least one of the articulation link and the articulation spindle, wherein the potentiometer is configured to measure the sensor signal reflective of at least one of a rotation of the articulation spindle and a displacement of the articulation link and to transmit the sensor signal to the microcontroller, wherein the microcontroller is configured to determine the angle as a function of the sensor signal.

6. A surgical instrument, comprising:
a handle portion;
a body portion extending distally from the handle portion and defining a first longitudinal axis;
an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
an articulation mechanism configured to articulate the articulating tool assembly, wherein the articulation mechanism includes:
a housing block configured to receive an articulation spindle rotatably housed therein;
an articulation link operatively coupled to the articulation spindle;
an articulation knob coupled to the articulation spindle for rotating the articulation spindle, wherein rotational motion of the articulation knob is translated into axial motion of the articulation link thereby articulating the articulating tool assembly; and
an articulation sensor assembly configured to transmit a sensor signal to a microcontroller which is configured to determine the angle of the articulating tool assembly, wherein the articulation sensor assembly includes an optical encoder sensor coupled to at least one of the articulation link and the articulation spindle, wherein the optical encoder sensor is configured to measure the sensor signal reflective of at least one of a rotation of the articulation spindle and a displacement of the articulation link and to transmit the sensor signal to the microcontroller, wherein the microcontroller is configured to determine the angle as a function of the sensor signal.

7. A surgical instrument, comprising:
a handle portion;
a body portion extending distally from the handle portion and defining a first longitudinal axis;
an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
an articulation mechanism configured to articulate the articulating tool assembly, wherein the articulation mechanism includes:
a housing block configured to receive an articulation spindle rotatably housed therein;
an articulation link operatively coupled to the articulation spindle;
an articulation knob coupled to the articulation spindle for rotating the articulation spindle, wherein rotational motion of the articulation knob is translated into axial motion of the articulation link thereby articulating the articulating tool assembly; and
an articulation sensor assembly configured to transmit a sensor signal to a microcontroller which is configured to determine the angle of the articulating tool assembly, wherein the articulation sensor assembly includes a photo sensor facing the articulation link, the photo sensor configured to illuminate the articulation link and to measure a light reflected from the articulation link and transmit the sensor signal corresponding to the measured reflected light to the microcontroller, wherein the microcontroller is configured to determine the angle as a function of a displacement of the articulation link based on the measured reflected light.

\* \* \* \* \*